United States Patent
Sakamoto et al.

(10) Patent No.: US 10,010,338 B2
(45) Date of Patent: Jul. 3, 2018

(54) MENISCECTOMY BY ARTHROENDOSCOPICAL SURGICAL METHOD

(71) Applicant: OLYMPUS CORPORATION, Hachioji-shi, Tokyo (JP)

(72) Inventors: Takamitsu Sakamoto, Hachioji (JP); Chie Onuma, Tama (JP); Ken Fujisaki, Sagamihara (JP); Kiichiro Sawada, Hachioji (JP); Kazuhiro Yoshida, Sagamihara (JP); Satoshi Takekoshi, Hachioji (JP); Sohei Ueda, Tokyo (JP); Yasuo Tanigami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 183 days.

(21) Appl. No.: 15/094,131

(22) Filed: Apr. 8, 2016

(65) Prior Publication Data
US 2017/0273709 A1    Sep. 28, 2017

Related U.S. Application Data

(63) Continuation-in-part of application No. 15/082,573, filed on Mar. 28, 2016.

(51) Int. Cl.
*A61B 17/32* (2006.01)
*A61B 17/00* (2006.01)

(52) U.S. Cl.
CPC ........ *A61B 17/320068* (2013.01); *A61B 17/00234* (2013.01); *A61B 17/32002* (2013.01); *A61B 2217/007* (2013.01)

(58) Field of Classification Search
CPC ...... A61B 17/320068; A61B 17/00234; A61B 17/32002; A61B 2217/007; A61B 1/043; A61B 1/0638; A61B 1/0676; A61B 1/00078; A61B 1/00009; A61B 1/00011; A61B 1/07; A61B 1/0684; A61B 1/05; A61B 1/317; A61B 1/00045; A61B 17/22012; A61B 2017/320072; A61B 2017/320073; A61B 17/3203; A61B 17/32037
See application file for complete search history.

(56) References Cited

U.S. PATENT DOCUMENTS

| | | | |
|---|---|---|---|
| 2010/0191173 A1* | 7/2010 | Kimura | A61B 17/320068 604/21 |
| 2012/0165848 A1* | 6/2012 | Slayton | A61N 7/02 606/169 |
| 2014/0114280 A1* | 4/2014 | Long | A61L 27/24 604/506 |
| 2015/0297073 A1* | 10/2015 | Nguyen | A61B 1/317 600/103 |
| 2017/0157271 A1* | 6/2017 | Mizuno | A61K 49/0034 |

* cited by examiner

*Primary Examiner* — Katrina Stransky
(74) *Attorney, Agent, or Firm* — Oliff PLC

(57) ABSTRACT

In an arthroendoscopical surgical method, a resection target area, which is emphasized by fluorescence with use of a fluorescent agent under excitation light, is identified on a meniscus, and a resection line or an imaginary resection line is drawn. Using an ultrasonic treatment tool and an arthroscope, the resection target area is resected by a probe which generates ultrasonic vibrations, based on the resection line or imaginary resection line under visible-light illumination, and an inclined resection surface is formed.

5 Claims, 11 Drawing Sheets

MENISCECTOMY BY ARTHROENDOSCOPICAL SURGICAL METHOD

CROSS-REFERENCE TO RELATED APPLICATIONS

This is a Continuation-in-Part of application Ser. No. 15/082,573 filed Mar. 28, 2016. The disclosure of the prior application is hereby incorporated by reference herein in its entirety.

BACKGROUND OF THE INVENTION

1. Field of the Invention

The present invention relates to a meniscectomy by an arthroendoscopical surgical method of treating a meniscus by using an ultrasonic treatment tool under arthroendoscopy.

2. Description of the Related Art

There is known a surgical operation which is generally called arthroendoscopical surgery. In the arthroendoscopical surgery, two or so small holes (external portals) are opened in the skin near an articulation. A rigid scope, which will serve as an arthroscope, and a therapeutic device, are inserted from the external portals (or portals). Treatment is performed while confirming video which is displayed on a monitor in a state in which the inside of the articulation is filled with perfusion liquid for articulation surgery.

For example, as disclosed in patent document 1 (US2015/0297073), the arthroendoscopical surgery is applicable to a surgical operation for administering surgical treatment to a meniscus. Endoscopical surgical methods using arthroscopes for menisci are generally classified into resection surgery which resects an injured denatured part of a meniscus, and suture surgery which sutures a denatured part. Either resection alone or suture is selected in consideration of a diagnosis result based on various conditions such as a form of tear, a part of tear, or the presence/absence of a blood flow in an injured part of a meniscus.

In conventional endoscopical meniscus surgery, the rigid scope or therapeutic device is inserted in an articulation from the above-described portal, and a denatured part of the meniscus is resented by a tool such as a punch or a shaver under observation by the arthroscope.

As will be described later, a meniscus includes an area in which blood flows and an area in which no blood flows. The area in which blood flows is further divided into an area where blood vessels are dense, and an area where blood vessels are sparse. On the outer peripheral side of the meniscus, there is a dense blood flow area A where many blood vessels (blood flows) exist. In the middle part, there is an area B [vascular area: sparse blood flow area] where blood flows, although fewer than in the area A [vascular area: dense blood flow area], exist. In the inner side of the area B, there is an area C [no-vascular area: no-blood-flow area] where no blood flow exists.

When the above-described denatured part of the meniscus is resented, it is required to exactly resect the denatured part, and to resect only the no-blood-flow area, so as not to cause damage to the other part.

However, in the resection by conventional art, there are considerable physical and chemical effects, such as overcutting of a resection surface and damage due to heat, and a surgeon has to pay close attention.

In addition, there are unclear points with respect to the condition of the end face of the displayed meniscus (e.g. whether a denatured part was resected or not, and whether vascular exists or not), and it is difficult to determine how far the resection should be performed, and skill is required for the determination.

Furthermore, FIG. 9A illustrates stress acting on a normal meniscus from a thighbone. On the other hand, as illustrated in FIG. 9B, by resection by a tool such as a punch, a cut surface, which is perpendicularly cut from an upper face of a curved surface of a meniscus, is formed, and a corner portion occurs. Stress tends to easily concentrate at the corner portion from the spherical contact surface of the thighbone.

When such a corner portion or irregularities occur on the cut surface, it is necessary to additionally perform resection or trimming for adjustment, thereby adjusting the cut surface of the meniscus. However, depending on the position of a treatment site, a sufficient treatment space cannot be acquired, and there may be a case in which proper adjustment cannot be implemented.

BRIEF SUMMARY OF THE INVENTION

According to an embodiment of the invention, a meniscectomy by an arthroendoscopical surgical method includes an identifying step of identifying a tear site of a meniscus having a curved shape; an administering step of administering a fluorescent agent to a vein; a confirmation step of confirming whether the tear site reaches a vascular area in an inside of the meniscus, by performing, after the administering step, fluorescence observation by causing the fluorescent agent to emit fluorescence with use of near-infrared light; and a setting step of forming, when the tear site does not reach the vascular area in the confirmation step, an inclined surface such that a resection target area includes the tear site and an inclination of the inclined surface increases from a central side toward an outside of the curved shape, and setting a boundary of the resection target area within a no-vascular area of the meniscus.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, an embodiment of the present invention will be described in detail with reference to the accompanying drawings.

Figure 1:
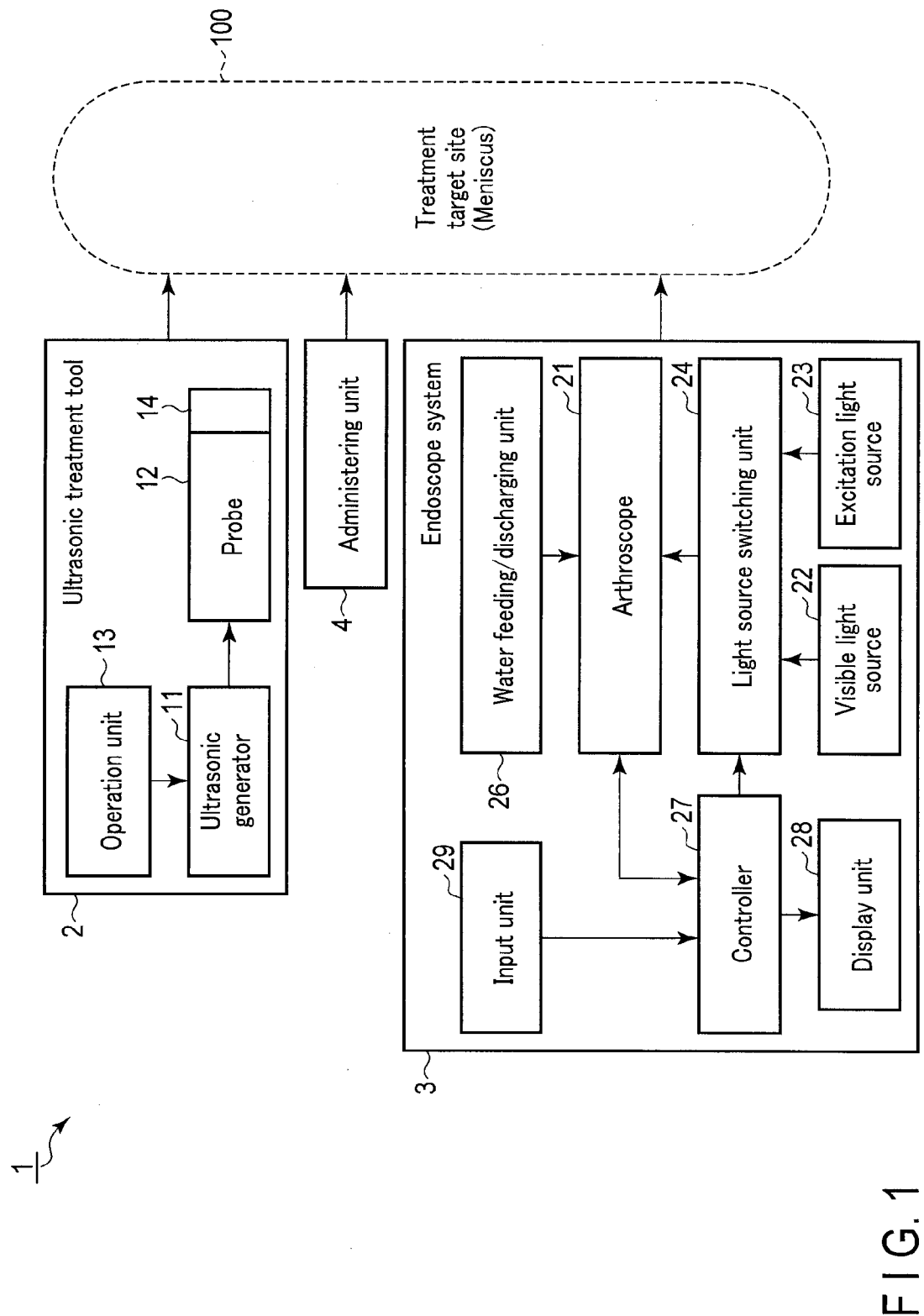
FIG. 1 is a view illustrating a configuration example of a surgery system including an ultrasonic treatment tool for implementing an arthroendoscopical surgical method according to an embodiment.

FIG. 1 illustrates a configuration example of a surgery system including an ultrasonic treatment tool for implementing an arthroendoscopical surgical method according to the embodiment. In the embodiment below, a description is given on the assumption that a treatment target site 100 of arthroendoscopical surgery is a meniscus by way of example.

A surgery system 1 of the present embodiment is composed of an ultrasonic treatment tool 2, an endoscope system 3 including an arthroscope, and an administering unit 4 configured to administer a fluorescent agent (the indocyanine green: ICG).

The ultrasonic treatment tool 2 includes an ultrasonic generator 11 configured to generate ultrasonic vibrations by an ultrasonic vibration element (e.g. a piezoelectric element); a probe 12 configured to transmit ultrasonic vibrations and perform cutting treatment of a treatment target site; and an operation unit 13 configured to execute driving control of the ultrasonic generator 11, and to on/off operate the generation of ultrasonic vibrations.

The probe 12 is an elongated rod-shaped member which extends in a longitudinal axis direction and has a diameter of about 2 mm to 4 mm, and includes a distal end portion and a proximal end portion. The proximal end portion of the probe 12 is coupled to the ultrasonic generator 11, and a treatment unit 14 is provided on the distal end portion.

The probe 12 transmits ultrasonic vibrations to the treatment unit 14, and performs resection treatment, with the treatment unit 14 being put in contact with the meniscus 100. The treatment unit 14 has, for example, a distal end shape of a rasp, or a hook shape with at least one projection.

It is possible to prepare in advance a plurality of treatment units 14 which are bent at different angles in a range of arbitrary angles of, e.g. 5° to 30°, relative to the longitudinal axis of the probe 12. A probe with a suitable angle is properly selected based on the treatment content which is administered to the treatment target site 100, and the positional relationship between the portal for inserting the treatment unit 14 and the location of treatment. In the meantime, the rasp is a hand-held surgical tool which includes a distal end portion having a surface with a plurality of projections or with raised file teeth, and is used for smoothing, grinding-in, or cutting of a tissue.

This ultrasonic treatment tool 2 performs resection by ultrasonic vibrations, that is, mechanical resection and resection by frictional heat by minute sliding movement, by putting the treatment unit 14, which is provided at the distal end of the probe 12 that generates ultrasonic vibrations, into contact with the meniscus that is the treatment target site 100. The ultrasonic treatment tool 2 can adjust the amount of cutting, in accordance with the pressure of pushing or the time of pushing of the treatment unit 14 upon the meniscus 100.

In this ultrasonic treatment tool 2, as regards the resection by ultrasonic vibrations of the probe that is supported at one end to the ultrasonic element, the amount of cutting can be adjusted in accordance with the degree (pushing pressure) of strength of pushing the distal-end treatment unit 14 upon the treatment site. Specifically, if the degree of contact is weak, the amount of cutting is small, and smoothing or fine cutting of the surface of the treatment target site is realized. If the degree of contact is strong, the amount of cutting increases. Accordingly, with the degree of cutting by a surgeon being reflected, efficient cutting, abscission, etc. are realized.

The endoscope system 3 includes an arthroscope 21 which is composed of a rigid scope that is a kind of endoscope; a visible light source 22 serving as an illumination light source, which is configured to radiate visible-light illumination; an excitation light source 23 configured to radiate excitation light (to be described later); a light source switching unit 24 configured to effect switching between the visible light and the excitation light, which are made incident on the arthroscope 21; a water feeding/discharging unit 26 configured to feed, discharge or perfuse perfusion water for articulation surgery, around the region including the meniscus 100 of the treatment target site; a controller 27 configured to control the entirety of the endoscope system 3; a display unit 28 configured to display surgery information including an imaged surgery condition; and an input unit 29 such as a keyboard or a touch panel. The present embodiment is configured such that the water feeding/discharging unit 26 feeds/discharges perfusion liquid for articulation surgery to/from the treatment site through the arthroscope 21. However, such a configuration may be adopted that the perfusion liquid for articulation surgery is fed/discharged from the ultrasonic treatment tool 2.

In addition, in the present embodiment, when the meniscus 100 is treated, a blood flow is visualized with fluorescence under infrared observation, and a resection line shown in FIG. 4B and FIG. 5B (to be described later) is judged and determined. Here, a fluorescent agent, in which infrared is easily absorbed, for instance, indocyanine green (ICG) (hereinafter referred to as "ICG"), is administered, and blood vessel or blood flow information is displayed with emphasis by using infrared which has good transmissivity. In this embodiment, as the fluorescent agent, ICG is described by way of example. However, other generally used fluorescent agents may be used, and the fluorescent agent is not limited to ICG.

The administering unit 8 shown in FIG. 1 is a syringe, and the syringe administers a fluorescent agent by intravenous injection or local injection (articular injection; indirect injection into a soft tissue), or administers a fluorescent agent into an articular cavity. The administered fluorescent agent is observed by being irradiated with excitation light at a time of identifying a tear site, and thereby the tear site can easily be visually recognized.

The fluorescent display by the ICG is used, for example, for a liver function test, a cardiovascular function test, or cerebral angiography, and no chemical change is suffered in the body. In addition, the concentration transition in the plasma decreases exponentially until about 15 minutes after administration, and then the decrease becomes gentle, and the ICG quickly disappears from the plasma.

Figure 2:
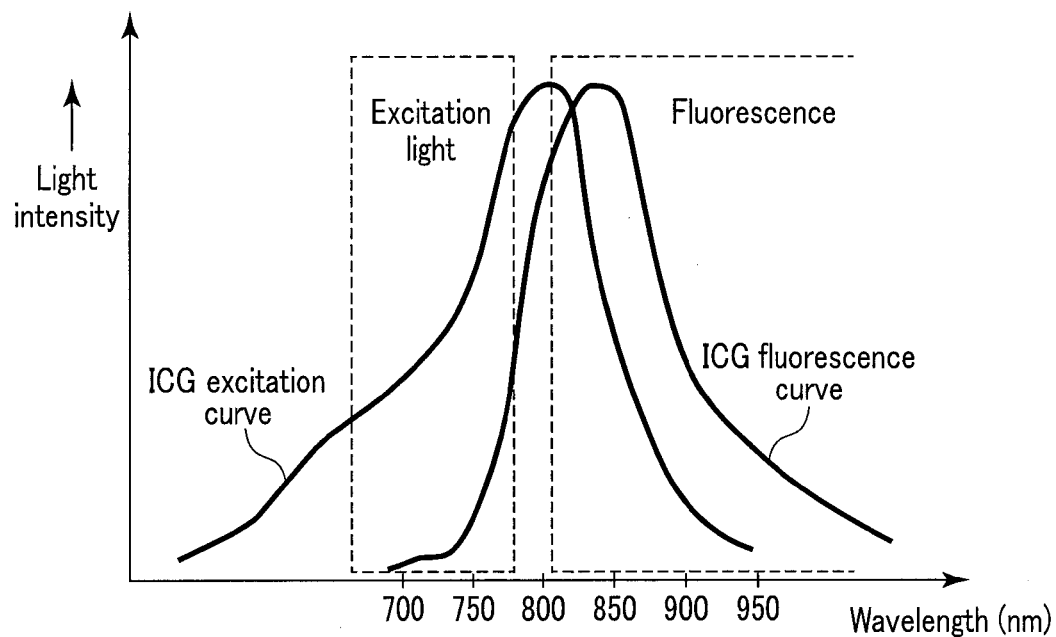
FIG. 2 is a view illustrating the relationship between wavelength and light intensity in excitation light and fluorescence.

As indicated by publicly known characteristics shown in FIG. 2, if the ICG is excited by irradiation of excitation light (ICG excitation curve) of near-infrared with wavelengths of 670 to 790 nm, fluorescence of near-infrared (ICG fluorescence curve) occurs with a peak wavelength of 835 nm which is longer than the wavelengths of 670 to 790 nm. By this fluorescence, a deep part of a living body (about 2 to 3 mm) can be observed. However, the fluorescence of the ICG is not directly visible to the human eye. Thus, by using a camera (CCD) which can photograph this wavelength band, the fluorescence can be observed as an image.

In addition, in the present embodiment, the configuration in which the light source can be switched by the light source switching unit 24 is included. During the observation, the same observation target can be observed while switching is made between infrared and visible light for use in normal observation.

Furthermore, in the embodiment, a touch panel is disposed on the display screen of the display unit 28, and a publicly known function is provided which enables drawing of a line on the screen by an input by the touch of a fingertip or pen, or by a cursor movement by a mouse. For example, while a surgeon is observing the meniscus on the fluorescence screen, the surgeon traces over the screen by the fingertip in order to distinguish a specific area where fluorescence occurs partly. Thereby, a line is drawn along the tracing. If this screen is changed to an observation screen with illumination by visible light, a transition occurs to the state in which the line is drawn over the image of the meniscus. If this line is set as a resection line for resection, an area to be resected can easily be judged.

Figure 3A:
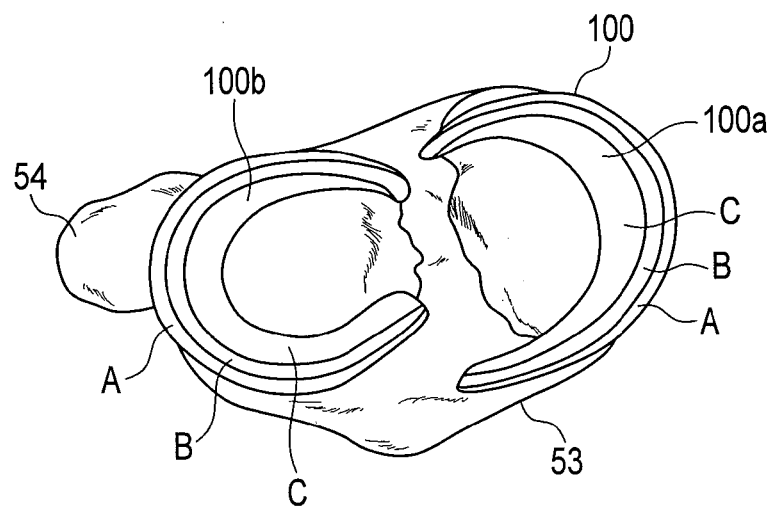
FIG. 3A is an external appearance view of a meniscus on the shinbone, as viewed from the thighbone side.
Figure 3B:
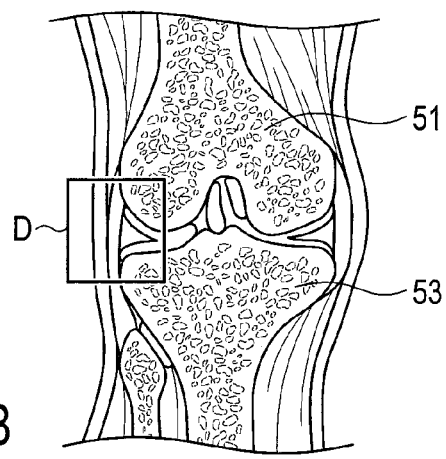
FIG. 3B is a view illustrating a cross section of a meniscus in a state in which the meniscus lies between the thighbone and shinbone.
Figure 3C:
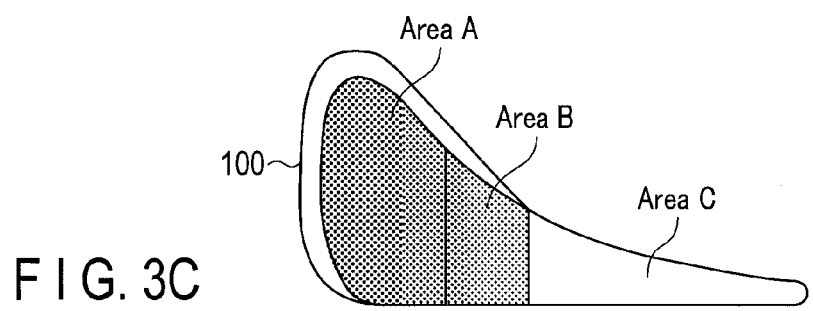
FIG. 3C is a view illustrating a cross section of the meniscus.

Here, referring to FIG. 3A, FIG. 3B and FIG. 3C, a description is given of the meniscus 100, the meniscus 100 to which a fluorescent agent was administered, and a resection area of the meniscus 100. FIG. 3A is an external appearance view of the meniscus 100 on the shinbone 53, as viewed from the thighbone 51 side. FIG. 3B is a view illustrating a cross section of the meniscus 100 in a state in which the meniscus 100 lies between the thighbone 51 and shinbone 53. FIG. 3G is a view illustrating a cross section of the meniscus 100.

As illustrated in FIG. 3A, the meniscus 100 is composed of two C-shaped cartilage tissues, which are disposed to be opposed to each other from both sides, namely the medial side and lateral side, like the shape of numeral "8", between the thighbone 51 and shinbone 53 of the knee joint of the leg. The meniscus 100 functions as a cushion and a stabilizer. The meniscus 100 is composed of a medial meniscus 100a and a lateral meniscus 100b. As illustrated in FIG. 3B, the upper surfaces of these menisci 100 extend along spherical surfaces of the thighbone 51, and the lower surfaces thereof extend along planar surfaces of the shinbone 53. Thus, as illustrated in FIG. 3C, in the cross section, the meniscus 100 has a less thickness on the inside, and a greater thickness toward the periphery.

On the outer peripheral side of the meniscus 100, there is a dense blood flow area A where many blood flows (blood vessels) exist. Toward the inside of the arc, there is an area B [vascular area: sparse blood flow area] where fewer blood flows than in the area A [vascular area: dense blood flow area] exist. In the inner side of the area B, there is an area C [no-vascular area: no-blood-flow area] where no blood flow exists. When the meniscus 100 is injured, the area A and area B, in which blood is flowing, can be regenerated. On the other hand, when the area C of the no-blood-flow area with no blood flow was injured, the area C cannot be regenerated, and thus only resection treatment is performed on the area C.

Figure 3D:
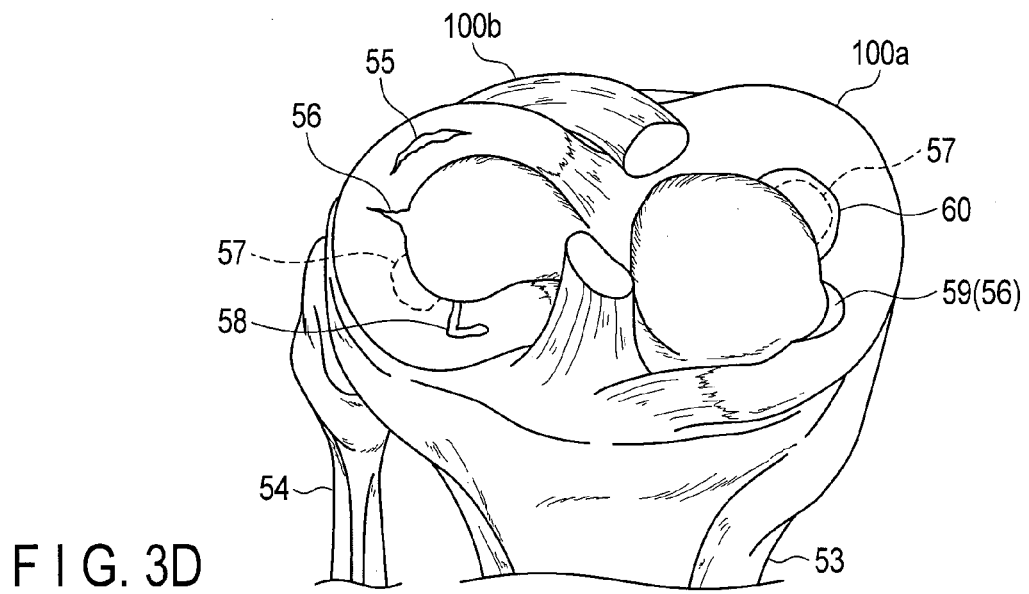
FIG. 3D is a view for describing damages occurring in the meniscus, and the state of the meniscus after resection treatment.

Here, FIG. 3D illustrates damages occurring in the lateral meniscus 100b, and the state of the medial meniscus 100a after resection treatment. In general terms, the lateral meniscus 100b includes a longitudinal tear 55 in which an inner cartilage tissue is torn in an up-and-down direction (longitudinally) along the longitudinal direction; a transverse tear 56 in which a tissue is torn like a cut from the inside toward the outside; a horizontal tear 57 in which an inner part is torn horizontally; and a flap tear 58 in which a tissue is torn longitudinally in an L shape. Resection treatment is performed on any of these damages, if the damage is a tear existing in the no-blood-flow area C.

Of these damages, in the case of the transverse tear 56, treatment of resecting apart around the tear site is performed, as will be described later. An upper resection part 59 of this resected part has such a cross-sectional shape that the upper resection part 59 is obliquely cut from the upper face, and has a shape with a missing part, when viewed from above. In addition, in the case of the horizontal tear 57, treatment of resecting an upper side portion of the horizontal tear is performed, as will be described later. An upper resection part 60 of this resected part has such a cross-sectional shape that the upper resection part 60 is obliquely resected and reduced in thickness, and the shape as a whole remains, when viewed from above.

Next, a description is given of ultrasonic resection treatment on a tear site.

As a first example, a description is given of a resection method at a time when the horizontal tear 57 occurred in the meniscus 100.

Figure 4A:
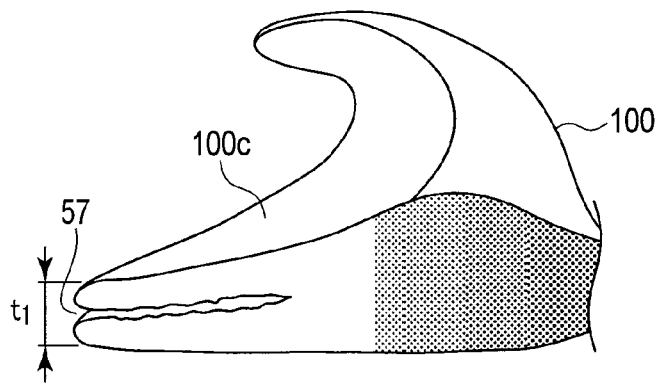
FIG. 4A is a cross-sectional view which illustrates a state in which a horizontal tear occurred in the meniscus.

FIG. 4A is a cross-sectional view which illustrates a state in which the horizontal tear 57 occurred in the meniscus 100. FIG. 4B is a conceptual view illustrating a resection line 61 or an imaginary resection line 62 being provided on the horizontal tear 57. FIG. 4C is a view illustrating a state of completion of treatment in which the tear site was resected.

As illustrated in FIG. 4A, a horizontal tear 57 occurs which extends from the area C of no blood flow of the meniscus 100 toward the inside. Probing (identification of tear site) is performed for setting a treatment target area of the meniscus 100. To begin with, using the administering unit 8, a fluorescent agent (ICG) is administered into a vein of a patient. Then, the arthroscope 21 is inserted from a portal provided in the knee, and excitation light is radiated from the excitation light source 23 to the meniscus 100. By the radiation of excitation light, the fluorescent agent, which is diffused in the meniscus 100, emits fluorescence. Since the density of the fluorescent agent becomes higher as the number of blood flows (blood vessels) is greater, this fluorescence becomes stronger where the number of blood flows is greater, and the fluorescence becomes weaker where the number of blood flows is smaller.

Specifically, in FIG. 3C, light emission is strong in the area A of the meniscus 100 displayed on the display unit 28, and light emission becomes weaker toward the area B. Further, substantially no light is emitted in the area C with no blood flow.

Figure 4B:
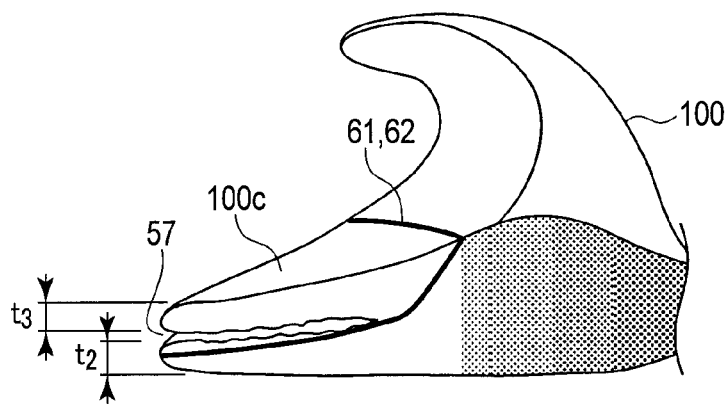
FIG. 4B is a conceptual view of an imaginary resection line being provided on the horizontal tear.
Figure 4C:
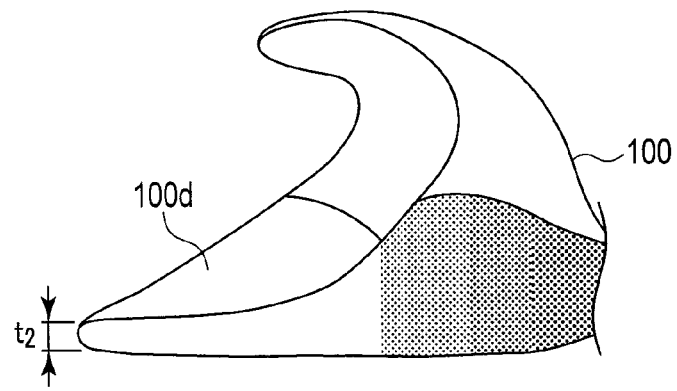
FIG. 4C is a view illustrating a state of completion of treatment in which a tear site was resected.

Then, as illustrated in FIG. 4B, a surgeon sets a resection line 61 or an imaginary resection line 62. To begin with, in a first method, with use of the ultrasonic treatment tool, the surgeon puts the treatment unit 14, which generates ultrasonic vibrations, into contact with the meniscus 100, while viewing an IR image under excitation light. Then, the surgeon moves the treatment unit 14, and directly makes marking on the meniscus 100 (makes a scar in the shape of a thread, or consecutive dots), thus drawing the resection line 61 and identifying a resection target area 100c.

In a second method, the surgeon traces over the touch panel of the display unit 28, which was subjected to sterilization treatment, by the fingertip, while viewing the IR image under excitation light, and draws an imaginary resection line 62 on the meniscus image on which the blood flow is displayed with emphasis, thereby identifying a three-dimensional resection target area 100c. The setting of the imaginary resection line 62 can be realized by mounting application software in the controller 27. At a time of drawing, the imaginary resection line 62 is drawn by being associated with the position information of the meniscus 100 on the screen. Thereby, even if the meniscus 100 moves on the screen, the imaginary resection line 62 follows the movement, and the line position on the meniscus 100 is maintained. In the meantime, since the resection line 61 is the marking which directly scars the meniscus 100, it is not preferable to re-draw the resection line 61. However, since the imaginary resection line 62 is drawn on the meniscus image, re-drawing is easy. In the description below, it is assumed that the resection line 61 and imaginary resection line 62 are identical, and the description is given by representatively using the imaginary resection line 62.

In the case of the horizontal tear 57, the imaginary resection line 62 is drawn in a manner to extend along the tear surface on the lower side (shinbone 53 side) and to then obliquely rise from an end face of the tear along the area B, and thus the resection target area 100c is set. Here, as illustrated in FIG. 4A, FIG. 4B and FIG. 4C, a tear site with a thickness t3 is resected from the meniscus 100 with an initial thickness t1 in which the horizontal tear 57 occurs. Thus, the thickness of the meniscus 100 after the resection decreases to a thickness t2.

Figure 9A:
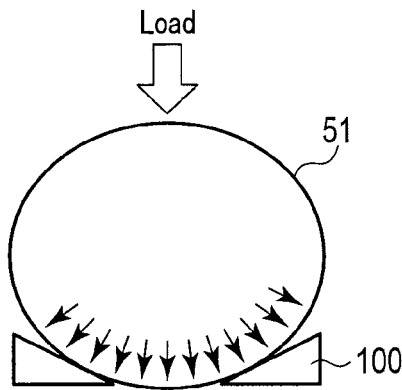
FIG. 9A is a conceptual view illustrating a state of stress applied to a normal meniscus from the thighbone.
Figure 9B:
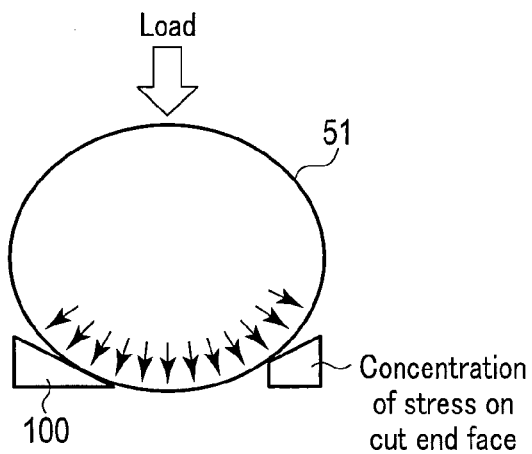
FIG. 9B is a conceptual view illustrating a state of stress applied from the thighbone to a meniscus which was resected by a conventional treatment tool such as a punch.
Figure 9C:
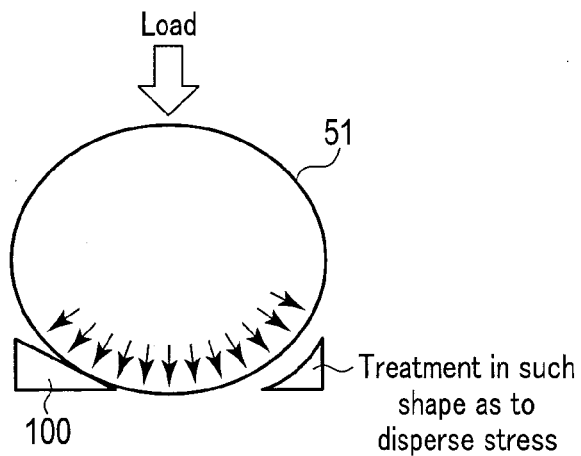
FIG. 9C is a conceptual view illustrating a state of stress applied from the thighbone to a meniscus having an oblique resection surface formed by the resection according to the embodiment.

As regards the setting of the imaginary resection line 62, it is important to obliquely set the imaginary resection line 62 so that no corner portion occurs on the upper surface of the meniscus 100 which will come in contact with the lower curved surfaces of the medial condyle of the thighbone and the lateral condyle of the thighbone after the resection. By the formation of an oblique resection surface 100d, concentration of stress can be prevented, as illustrated in FIG. 9C.

Secondly, a description is given of ultrasonic resection treatment at a time when a transverse tear 56 occurred in the meniscus 100.

Figure 5A:
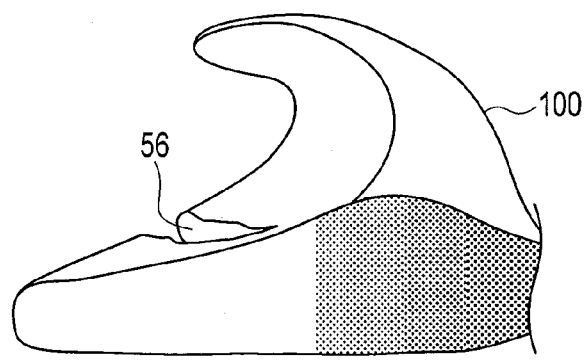
FIG. 5A is a cross-sectional view illustrating a state in which a transverse tear occurred in the meniscus.

FIG. 5A is a cross-sectional view illustrating a state in which the transverse tear 56 occurred in the meniscus 100. FIG. 53 is a conceptual view illustrating an imaginary resection line being provided on the transverse tear 56. FIG. 5C is a view illustrating a state of completion of treatment in which the transverse tear 56 was resected.

As illustrated in FIG. 5A, a transverse tear 56 by a tear in an up-and-down direction occurs toward the inside from the no-blood-flow area C of the meniscus 100. Probing (identification of tear site is performed for setting a resection target area of the meniscus 100.

To begin with, using the administering unit 8, a fluorescent agent (ICG) is administered into a vein of a patient. Then, the arthroscope 21 is inserted from the portal provided in the knee, and excitation light is radiated from the excitation light source 23 to the meniscus 100. By the radiation of excitation light, the fluorescent agent, which is diffused in the meniscus 100, emits fluorescence, as described in the above-described first example.

Figure 5B:
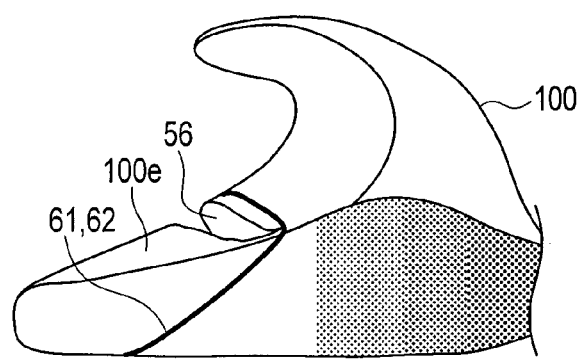
FIG. 5B is a conceptual view illustrating an imaginary resection line being provided on the transverse tear.
Figure 5C:
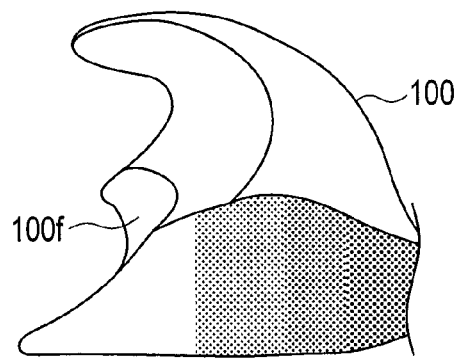
FIG. 5C is a view illustrating a state of completion of treatment in which the transverse tear was resected.

The surgeon traces over the meniscus image on which the blood flows are displayed with emphasis, and draws and inputs an imaginary resection line 62, as shown in FIG. 5B, from the touch panel. Thereby, the surgeon identifies a three-dimensional resection target area 100c. Here, the surgeon draws the imaginary resection line 62 in a manner to surround the transverse tear 56 from the area A side, and sets a resection target area 100e. When this imaginary resection line 62 is drawn, the imaginary resection line 62 is set such that, after the resection, there remains no transverse tear 56 on the lower side of the meniscus 100 which comes in contact with the shinbone 53, and a resection surface 100f has an inclination as described above.

Next, the procedure of treatment of the meniscus using the ultrasonic treatment tool is described.

Figure 6:
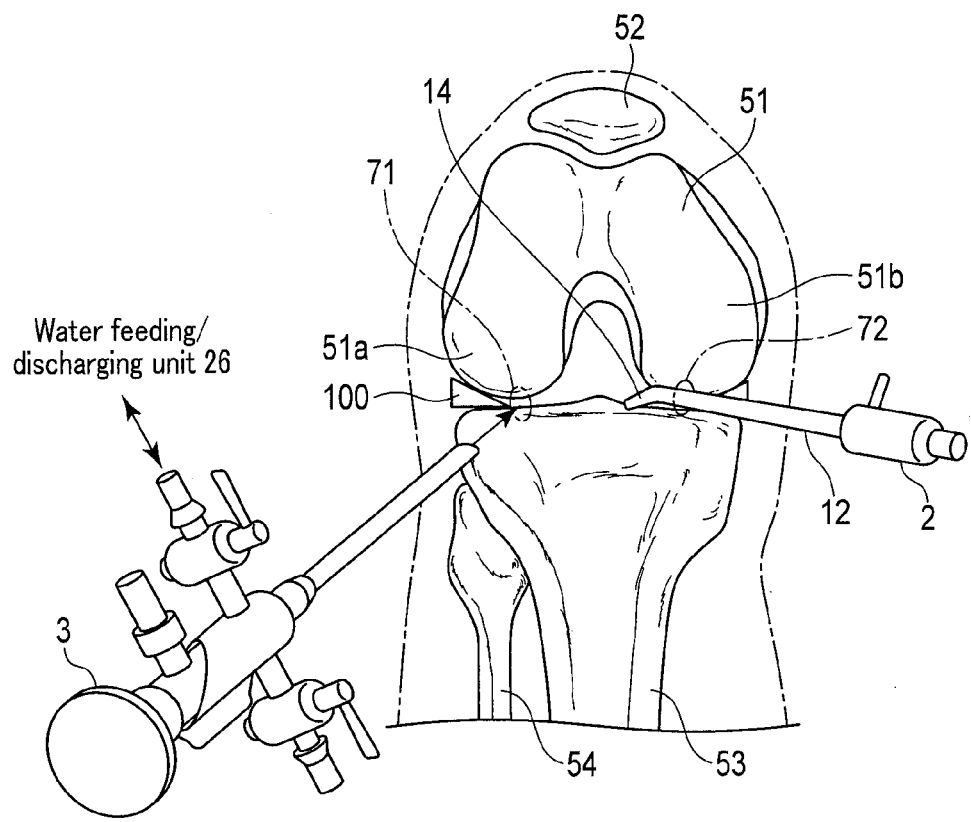
FIG. 6 is a view which conceptually illustrates a state of surgery in which an arthroscope and an ultrasonic treatment tool are inserted.
Figure 7:
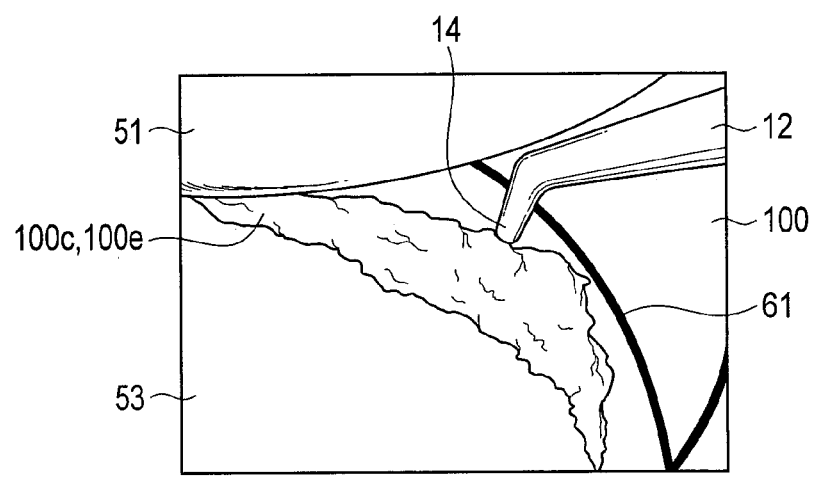
FIG. 7 is a view illustrating a state in which a resection target area of a meniscus is resected by the ultrasonic treatment tool, while being viewed from the arthroscope.

Here, FIG. 6 is a view which conceptually illustrates a state of surgery in which the arthroscope and ultrasonic treatment tool are inserted. FIG. 7 is a view illustrating a state in which a resection target area of the meniscus is resected by the ultrasonic treatment tool, while being viewed from the arthroscope. FIGS. 8A, 8B, 8C and 8D are flowcharts illustrating procedures of resection treatment of the meniscus. In addition, FIG. 9A is a conceptual view illustrating a state of stress applied to a normal meniscus from the thighbone. FIG. 9B is a conceptual view illustrating a state of stress applied from the thighbone to a meniscus which was resected by a conventional treatment tool such as a punch. FIG. 9C is a conceptual view illustrating a state of stress applied from the thighbone to a meniscus having an oblique resection surface formed by the resection according to the embodiment.

As described above, depending on the states of tear sites occurring in the meniscus 100, there is a tear site in a tear state which can be determined without administration of the fluorescent agent, and there is a tear site in a tear state which cannot be determined without administration of the fluorescent agent, and there is a tear site on which the resection line is set, and there is a tear site on which the resection line is not set. Surgery steps of combinations of these will be described.

Figure 8A:
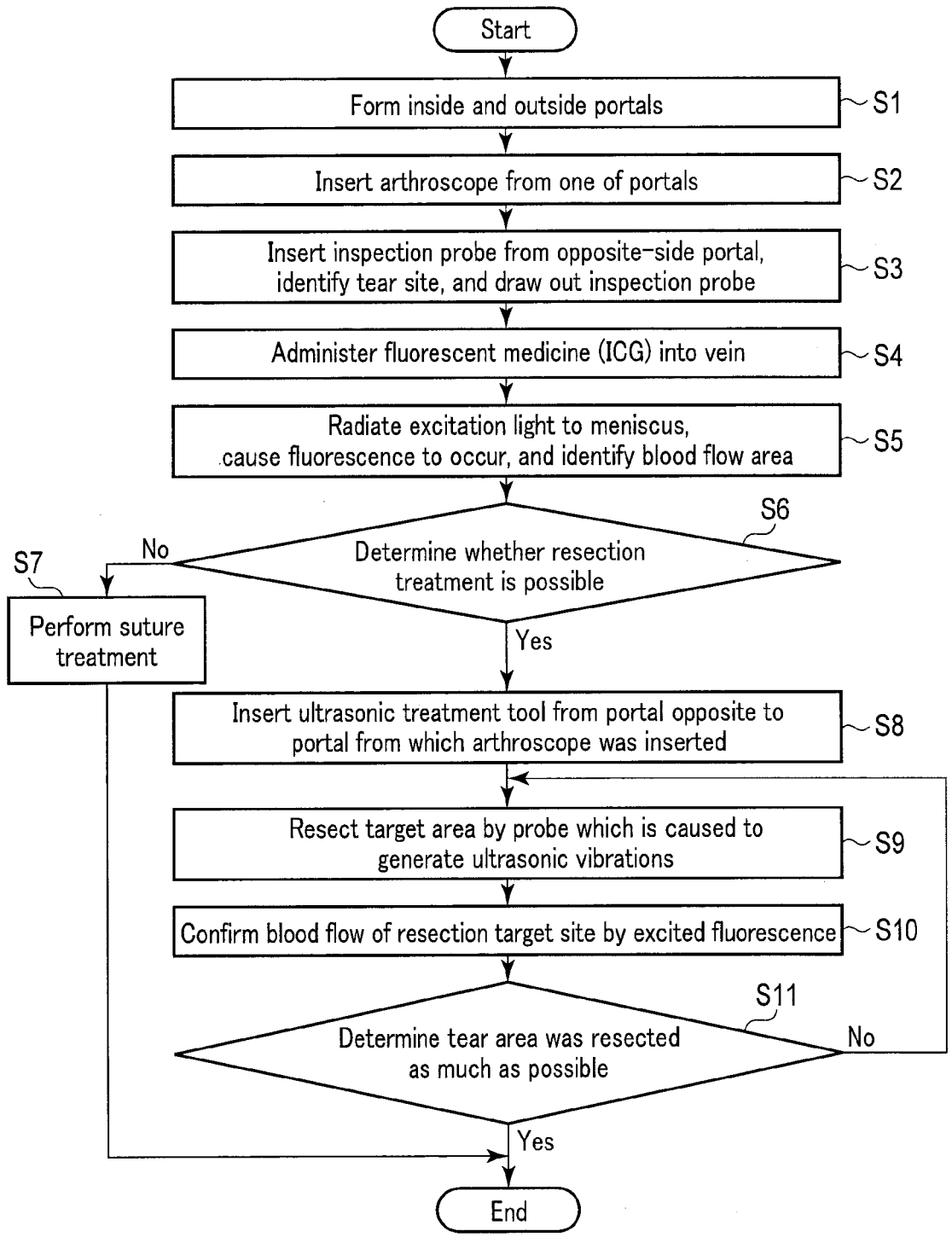
FIG. 8A is a flowchart illustrating surgery steps of resecting a resection target area, with no fluorescent agent being administered into an articular cavity, and with no resection line being set.
Figure 8B:
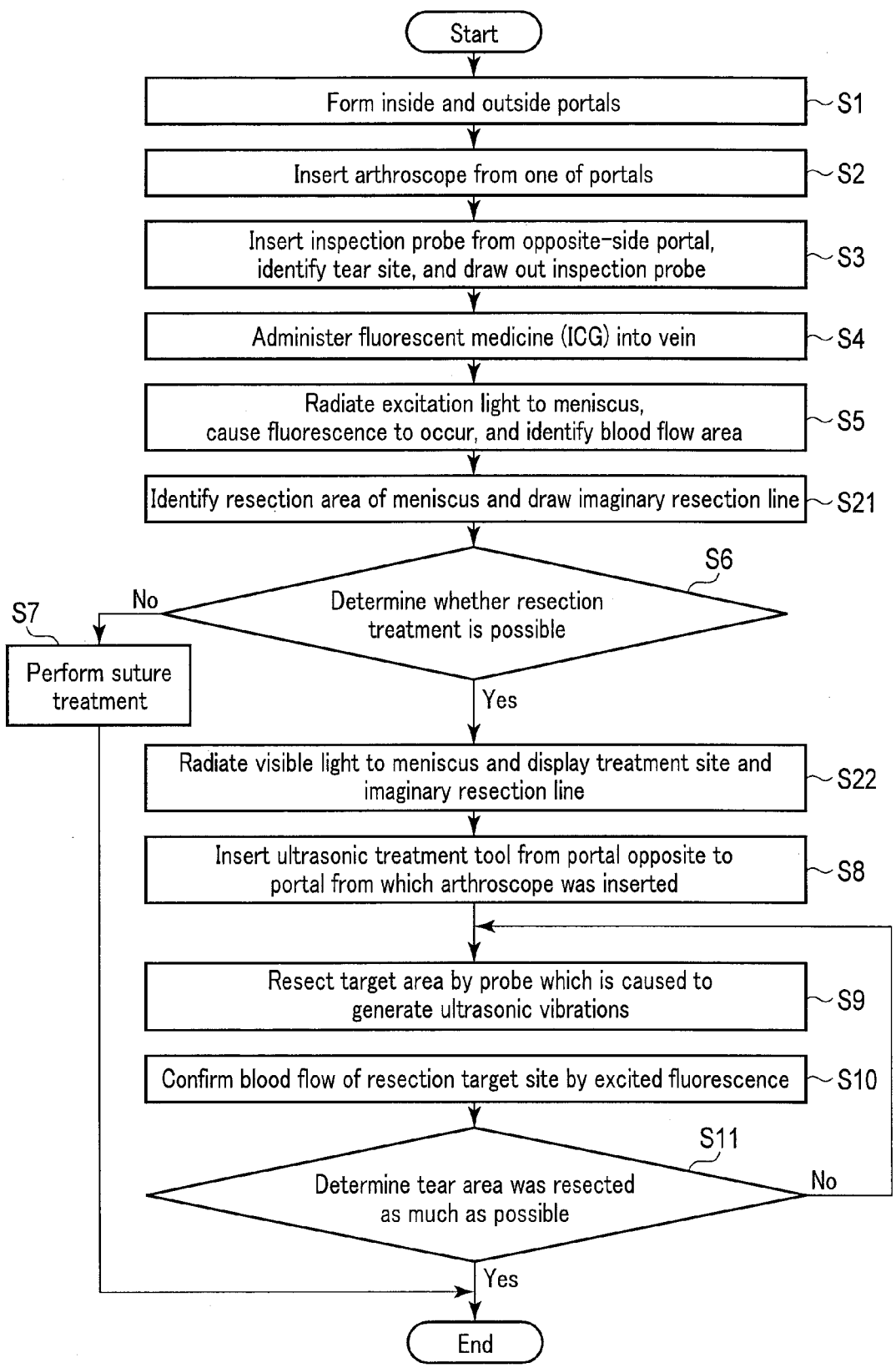
FIG. 8B is a flowchart illustrating surgery steps of resecting a resection target area, with no fluorescent agent being administered into an articular cavity, and with a resection line being set.
Figure 8C:
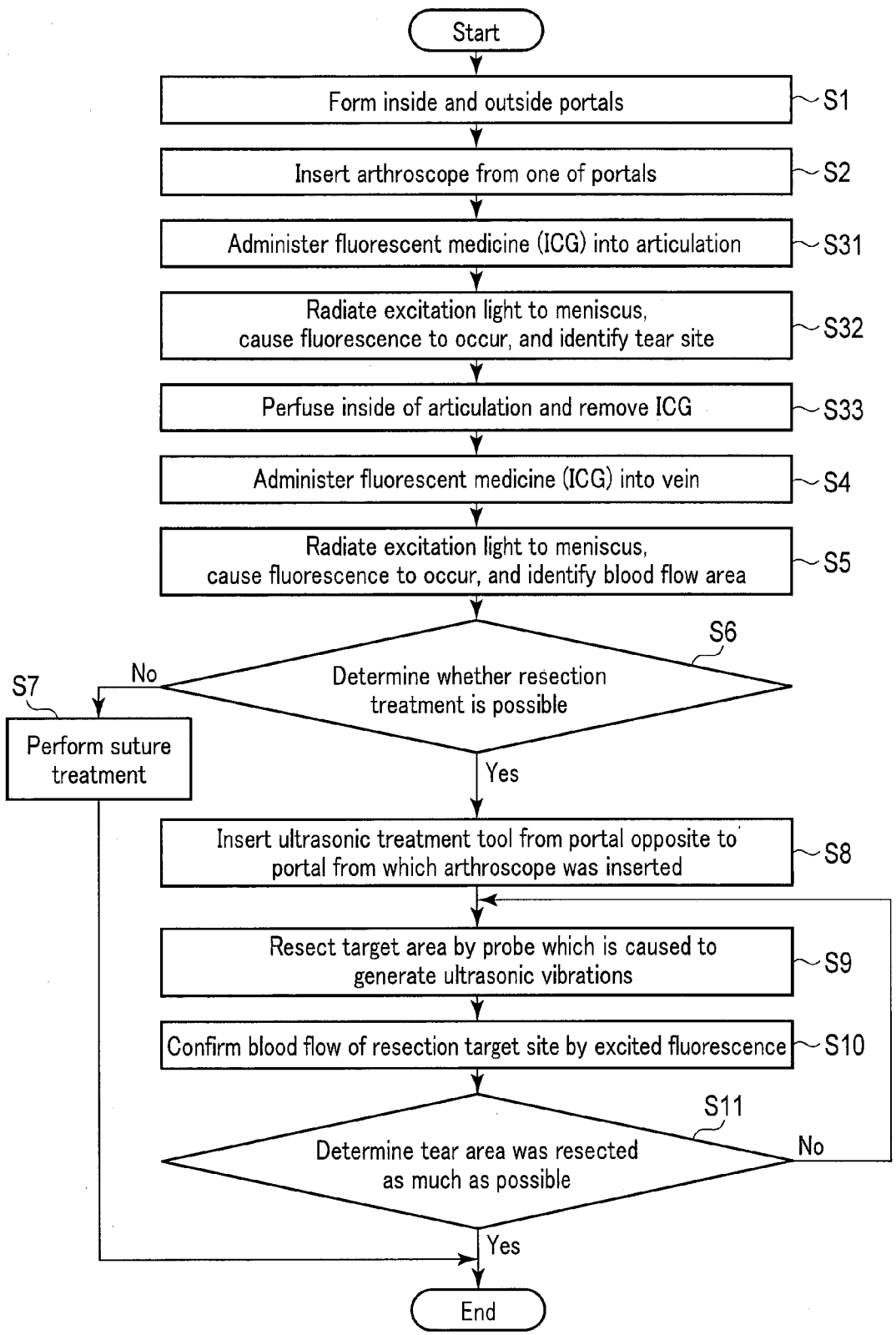
FIG. 8C is a flowchart illustrating surgery steps of resecting a resection target area, with a fluorescent agent being administered, and with no resection line being set in an articular cavity.
Figure 8D:
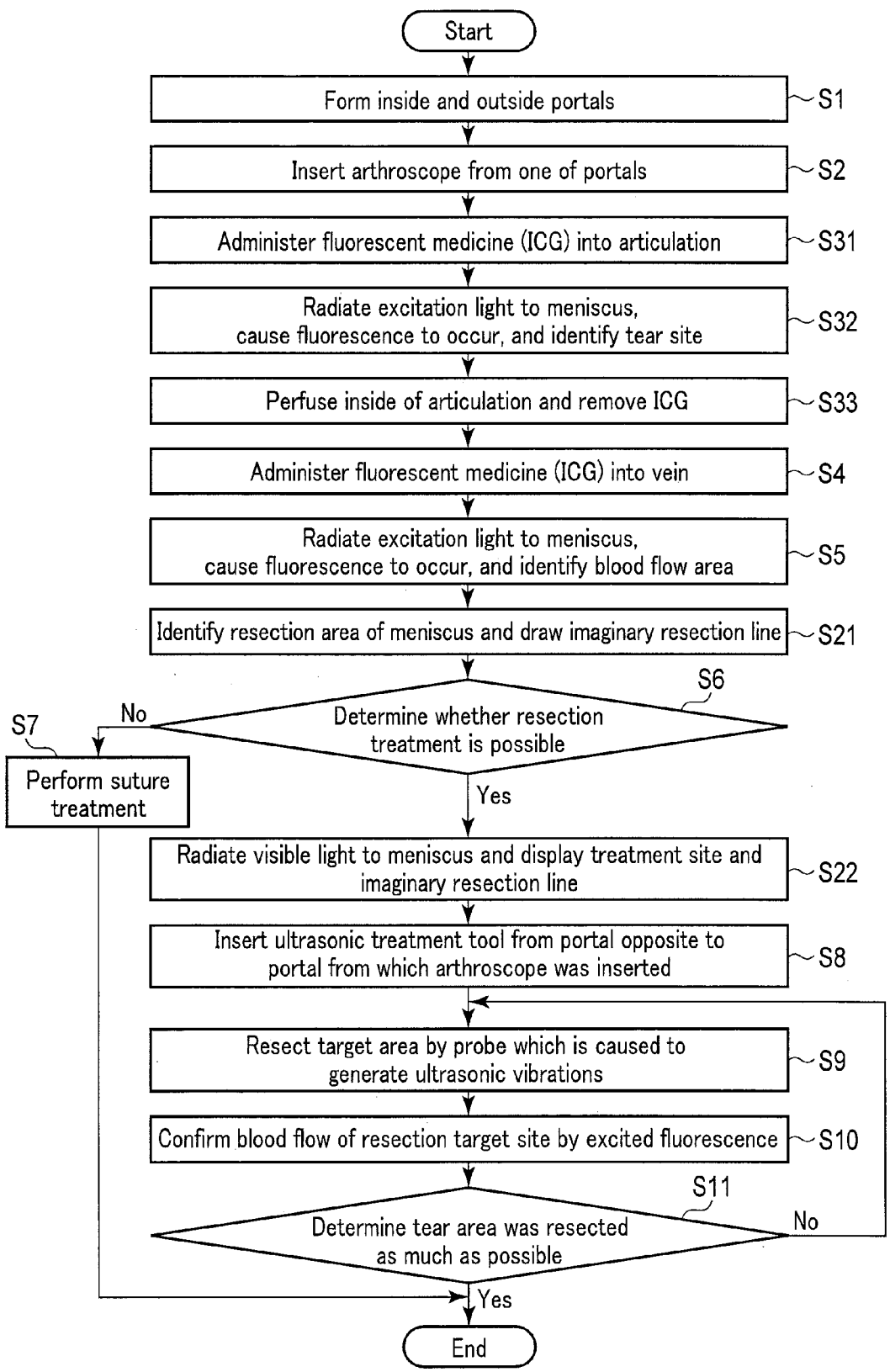
FIG. 8D is a flowchart illustrating surgery steps of resecting a resection target area, with a fluorescent agent being administered, and with a resection line being set in an articular cavity.

In the present embodiment, FIG. 8A is a flowchart illustrating surgery steps of resecting a resection target area, with no fluorescent agent being administered into an articular cavity, and with no resection line being set. FIG. 8B is a flowchart illustrating surgery steps of resecting a resection target area, with no fluorescent agent being administered into an articular cavity, and with a resection line being set. FIG. 8C is a flowchart illustrating surgery steps of resecting a resection target area, with a fluorescent agent being administered, and with no resection line being set in an articular cavity. FIG. 8D is a flowchart illustrating surgery steps of resecting a resection target area, with a fluorescent agent being administered, and with a resection line being set in an articular cavity.

Referring to the flowchart of FIG. 8A, a description is given of the surgery steps of resection, with no fluorescent agent being administered into an articular cavity, and with no resection line being set.

To start with, as illustrated in FIG. 6, a lateral parapatellar portal 71 (hereinafter referred to as "outside portal") for inserting the arthroscope 21 and a medial parapatellar portal 72 (hereinafter referred to as "inside portal") for inserting the ultrasonic treatment tool 2 are formed between the lower sides of the lateral condyle 51a and medial condyle 51b and the meniscus 100 of the bent knee of the patient (step S1). The arthroscope 21 is inserted from one portal (step S2), and an inspection probe is inserted from the other portal to identify a tear site, and the inspection probe is drawn out (step S3). This inspection probe is an inspection device for confirming a tear by putting a pointed end portion thereof in contact with a denatured part or the like.

A fluorescent agent (ICG) is administered to a vein of a patient by using the administering unit 8 (step S4).

By radiating excitation light from the excitation light source 23, fluorescence is caused to occur, and the blood vessel and blood flow information in the meniscus 100 are displayed with emphasis on the display unit 28, and a blood flow area is identified (step S5).

Based on this blood flow area, the form and size of a tear site, and the denaturing of the meniscus are examined, and it is determined whether resection treatment with no application of suture surgery is possible (YES) or not (NO) (step S6).

In this determination, if it is determined that suture treatment is performed (NO), tear parts are joined and subjected to suture treatment with a suture thread (step S7). However, if it is determined that resection treatment is performed (YES), the ultrasonic treatment tool 2 is inserted from the portal in which the arthroscope 21 is not inserted (step S8).

Next, switching of illumination light is made by the light source switching unit 24, and an observation image of a treatment site under visible-light illumination is imaged and displayed on the display unit 28. Thereafter, perfusion liquid for articulation surgery is fed and perfused from the water feed/discharge unit 26 through the arthroscope 21, up to a state in which the periphery of the treatment site is filled with the perfusion liquid. While confirming the position of the treatment site by viewing the observation image displayed on the display unit 28, the treatment unit 14 at the distal end of the probe 12, which is caused to generate ultrasonic vibrations, is abutted on the site of resection of the meniscus 100, and resection is performed (step S9). In this resection, as illustrated in FIG. 7, with use of the treatment unit 14, a surface, which has an oblique shape and is as smooth as possible, is formed such that the stress on the resection surface 100d of the meniscus 100 is dispersed.

During the resection treatment, at a stage when the resection has progressed to some degree, the resection is temporarily suspended and the visible light is switched to the excitation light by the light source switching unit 24. By fluorescence excited once again, the resection target site is caused to emit fluorescence, and the blood flow is confirmed (step S10).

The residual of the tear area is confirmed based on the blood flow, and switching is made back to the visible-light illumination by the light source switching unit 24. Thereafter, the resection treatment is continued by the treatment unit 14, and the tear area is resected as much as possible. It is determined whether the tear area was resected as much as possible (step S11). If the resection is not completed (NO), the process returns to step S9. If the resection is completed (YES), the series of resection treatment steps is finished.

Referring to the flowchart of FIG. 8B, a description is given of the surgery steps of resection, with no fluorescent agent being administered, and with a resection line being set. Incidentally, in the description below, the surgery steps, which are identical in treatment content to the above-described surgery steps of FIG. 8A, are denoted by the same reference numerals of surgery steps, and a detailed description thereof is omitted.

To start with, the portals 71 and 72 for inserting the arthroscope 21 and ultrasonic treatment tool 2 are formed (step S1). The arthroscope 21 is inserted from one portal (step S2), and the inspection probe is inserted from the other portal to identify a tear site, and the inspection probe is drawn out (step S3). A fluorescent agent (ICG) is administered to the vein of the patient by using the administering unit 8 (step S4).

Next, by radiating excitation light from the excitation light source 23, fluorescence is caused to occur, and the blood vessel and blood flow information in the meniscus 100 are displayed with emphasis on the display unit 28, and a blood flow area is identified (step S5).

Subsequently, probing (identification of tear site) is performed for the meniscus 100 which is displayed with emphasis on the display unit 28. By this probing, a resection target area 100c or 100e of the meniscus 100 is identified three-dimensionally, the touch panel of the screen of the display unit 28 is traced by the fingertip, and the imaginary resection line 62 shown in FIG. 4B or FIG. 5B is drawn (step S21).

The blood flow in the meniscus is evaluated from the image of the meniscus 100 on which this imaginary resection line 62 is drawn, and the form and size of the tear, and the denaturing of the meniscus are examined, and it is determined whether resection treatment with no application of suture surgery is possible or not (step S6). In this determination, if it is determined that suture treatment is performed (NO), tear parts are joined and subjected to suture treatment with a suture thread (step S7). However, if it is determined that resection treatment is performed (YES), switching is made from the excitation light source 23 to visible light source 22 by the light source switching unit 24, and an observation image of a treatment site under visible-light illumination is imaged and displayed on the display unit 28 (step S22). At this time, the display of the imaginary resection line 62 remains on the screen, and is superimposedly displayed on the image of the meniscus which is illuminated with visible light.

Next, the ultrasonic treatment tool 2 is inserted from the portal in which the arthroscope 21 is not inserted (step S8). Thereafter, perfusion liquid for articulation surgery is fed and perfused from the water feed/discharge unit 26 through the arthroscope 21, up to a state in which the periphery of the treatment site is filled with the perfusion liquid. While confirming the position of the treatment site by viewing the observation image displayed on the display unit 28, the treatment unit 14 at the distal end of the probe 12, which is caused to generate ultrasonic vibrations, is abutted on the site of resection of the meniscus 100, and resection is performed such that the resection surface 100d becomes a surface which has an oblique shape and is as smooth as possible (step S9). During the resection treatment, at a stage when the resection has progressed to some degree, switching is made back to the excitation light, the resection target site is caused to emit fluorescence, and the blood flow is confirmed (step S10).

Thereafter, it is determined whether the tear area was resected as much as possible by the resection treatment (step S11). If the resection is not completed (NO), the process returns to step S9. If the resection is completed (YES), the series of resection treatment steps is finished.

Referring to the flowchart of FIG. 8C, a description is given of the surgery steps of resection, with a fluorescent agent being administered, and with no resection line being set in the articular cavity. Incidentally, in the description below, the surgery steps, which are identical in treatment content to the above-described surgery steps of FIG. 8A, are denoted by the same reference numerals of surgery steps, and a detailed description thereof is omitted.

To start with, the portals 71 and 72 for inserting the arthroscope 21 and ultrasonic treatment tool 2 are formed (step S1). The arthroscope 21 is inserted from one portal (step S2).

Next, a fluorescent agent (ICG) is administered into the articulation (step S31). By radiating excitation light to the meniscus 100, fluorescence is caused to occur, and a tear site is identified (step S32). After the identification, the inside of the articulation is perfused with perfusion liquid from the water feed/discharge unit 26 through the arthroscope 21, and the fluorescent agent (ICG) is discharged and removed (step S33).

Subsequently, a fluorescent agent (ICG) is administered to the vein of the patient by using the administering unit 8 (step S4). By radiating excitation light from the excitation light source 23, fluorescence is caused to occur, and the blood vessel and blood flow information in the meniscus 100 are displayed with emphasis on the display unit 28, and a blood flow area is identified (step S5).

Based on the blood flow area, it is determined whether resection treatment with no application of suture surgery is possible or not (step S6). In this determination, if it is determined that suture treatment is performed (NO), tear parts are joined and subjected to suture treatment with a suture thread (step S7). However, if it is determined that resection treatment is performed (YES), the ultrasonic treatment tool 2 is inserted from the portal in which the arthroscope 21 is not inserted (step S8).

Next, by the probe 12 which is caused to generate ultrasonic vibrations, the resection target site of the meniscus 100 is resected so as to form an oblique, smooth surface (step S9). During the resection treatment, at a stage when the resection has progressed to some degree, switching is made back to the excitation light, the resection target site is caused to emit fluorescence, and the blood flow is confirmed (step S10). Thereafter, it is determined whether the tear area was resected as much as possible by the resection treatment (step S11). If the resection is not completed (NO), the process returns to step S9. If the resection is completed (YES), the series of resection treatment steps is finished.

Referring to the flowchart of FIG. 8D, a description is given of the surgery steps of resection, with a fluorescent agent being administered, and with a resection line being set in the articular cavity. Incidentally, in the description below, the surgery steps, which are identical in treatment content to the above-described surgery steps of FIG. 8A, are denoted by the same reference numerals of surgery steps, and a detailed description thereof is omitted.

To start with, the portals 71 and 72 for inserting the arthroscope 21 and ultrasonic treatment tool 2 are formed (step S1). The arthroscope 21 is inserted from one portal (step S2).

Next, a fluorescent agent (ICG) is administered into the articulation (step S31). By radiating excitation light to the meniscus 100, fluorescence is caused to occur, and a tear site is identified (step S32). After the identification, the inside of the articulation is perfused with perfusion liquid from the water feed/discharge unit 26 through the arthroscope 21, and the fluorescent agent (TOG) is discharged and removed (step S33).

Subsequently, a fluorescent agent (ICG) is administered to the vein of the patient by using the administering unit 8 (step S4). By radiating excitation light from the excitation light source 23, fluorescence is caused to occur, and the blood vessel and blood flow information in the meniscus 100 are displayed with emphasis on the display unit 28, and a blood flow area is identified (step S5).

Subsequently, probing (identification of tear site) is performed for the meniscus 100 which is displayed with emphasis on the display unit 28. By this probing, a resection target area 100c or 100e of the meniscus 100 is identified three-dimensionally, the touch panel of the screen of the display unit 28 is traced by the fingertip, and the imaginary resection line 62 shown in FIG. 4B or FIG. 5B is drawn (step S21).

The blood flow in the meniscus is evaluated from the image of the meniscus 100 on which this imaginary resection line 62 is drawn, and the form and size of the tear, and the denaturing of the meniscus are examined, and it is determined whether resection treatment with no application of suture surgery is possible or not (step S6). In this determination, if it is determined that suture treatment is performed (NO), tear parts are joined and subjected to suture treatment with a suture thread (step S7). However, if it is determined that resection treatment is performed (YES), switching is made from the excitation light source 23 to visible light source 22 by the light source switching unit 24, and an observation image of a treatment site under visible-light illumination is imaged and displayed on the display unit 28 (step S22). At this time, the display of the imaginary resection line 62 remains on the screen, and is superimposedly displayed on the image of the meniscus which is illuminated with visible light.

Next, the ultrasonic treatment tool 2 is inserted from the portal in which the arthroscope 21 is not inserted (step S8). Thereafter, perfusion liquid for articulation surgery is fed and perfused from the water feed/discharge unit 26 through the arthroscope 21, up to a state in which the periphery of the treatment site is filled with the perfusion liquid. While confirming the position of the treatment site by viewing the observation image displayed on the display unit 28, the treatment unit 14 at the distal end of the probe 12, which is caused to generate ultrasonic vibrations, is abutted on the site of resection of the meniscus 100, and resection is performed such that the resection surface 100d becomes a surface which has an oblique shape and is as smooth as possible (step S9). During the resection treatment, at a stage when the resection has progressed to some degree, switching is made back to the excitation light, the resection target site is caused to emit fluorescence, and the blood flow is confirmed (step S10).

Thereafter, it is determined whether the tear area was resected as much as possible by the resection treatment (step S11). If the resection is not completed (NO), the process returns to step S9. If the resection is completed (YES), the series of resection treatment steps is finished.

In this example, the resection line is the imaginary resection line 62 which is drawn on the display screen of the display unit 28. However, when the resection line 61 is directly drawn on the meniscus 100, the ultrasonic treatment tool 2 is inserted in the inside portable 72 in step S21, and the resection line 61 is drawn by abutting the distal end of the probe, which generates ultrasonic vibrations, upon the meniscus 100, thereby identifying the resection target area 100c or 100e.

The arthroendoscopical surgical method of the above-described embodiment has the following advantageous effects.

In the arthroendoscopical surgical method of the embodiment, resection can be performed by using the ultrasonic treatment tool, and the resection line can be set up to a boundary of the vascular area, since the fluorescent agent (ICG) is administered to the vein of the patient when the resection target area is set, and the blood flow area (vascular area) of the meniscus 100, which emits fluorescence, is confirmed.

The imaginary resection line, which was set under fluorescence, is superimposedly displayed on the image of the meniscus 100 which is illuminated by visible light in the surgical environment. Thus, the actual resection target area can be easily understood. In addition, since the setting of the imaginary resection line can be made by simply tracing over the displayed observation image, the imaginary resection line can be set easily in a short time.

The treatment unit, to which an end portion of the ultrasonic treatment tool is fixed, is caused to generate microvibration, thereby to perform resection treatment. Thus, the surgeon can adjust the amount of cutting by the pressure of pushing or the time of pushing of the treatment unit upon the resection site. The surgeon can freely adjust the amount of cutting, between the resection/abscission treatment with strong pushing, and the planarization treatment for planarizing the resection surface with weak pushing, and realizes efficient resection, abscission, etc. Since the speed of resection can be adjusted, a resection target area with even a complicated shape can be finely resected.

The cutting by the probe, which generates ultrasonic vibration, is not the treatment by a heat source such as by an electric scalpel. Thus, the treatment can be performed without raising the temperature of the treatment site, and thermal damage to the treatment site can be prevented.

Cutting progresses in the direction in which the probe is pushed. This is different from the cutting in the axial direction by a rotary shaft, such as by an electric drill, or the cutting utilizing the periphery of a rotating drill, which may involve other parts. Compared to the adjustment of the cutting amount based on conventional manual adjustment, the adjustment is very easy, and the fatigue of the surgeon is alleviated.

By the treatment used for the meniscus 100, the resection surface of the meniscus can be formed in an oblique shape, and stress acting from the thighbone can be dispersed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A meniscectomy by an arthroendoscopical surgical method, comprising:
    identifying a tear site of a meniscus having a curved shape;
    administering a fluorescent agent to a vein;
    confirming whether the tear site reaches a vascular area in an inside of the meniscus, by performing, after the administering step, fluorescence observation by causing the fluorescent agent to emit fluorescence with use of near-infrared light; and
    setting, when the tear site does not reach the vascular area in the confirming, an inclined surface such that a resection target area includes the tear site and an inclination of the inclined surface increases from a central side toward an outside of the curved shape, and setting a boundary of the resection target area within a no-vascular area of the meniscus.

2. The meniscectomy by an arthroendoscopical surgical method of claim 1, further comprising marking the resection target area which was set in the setting.

3. The meniscectomy by an arthroendoscopical surgical method of claim 2, wherein the marking includes drawing the resection target area of the meniscus on the meniscus by a probe of an ultrasonic treatment tool, the probe generating ultrasonic vibrations.

4. The meniscectomy by an arthroendoscopical surgical method of claim 2, wherein the marking includes displaying an imaged image of the meniscus on a display screen which is equipped with a touch panel, and marking, from the touch panel, an imaginary resection line on the displayed resection target area including the tear site in association with position information of the image of the meniscus.

5. The meniscectomy by an arthroendoscopical surgical method of claim 2, further comprising:
    administering a fluorescent agent to an articular cavity and a vein; and
    observing a fluorescence by causing the fluorescent agent to emit fluorescence with use of near-infrared light.

* * * * *